United States Patent
Spottiswoode et al.

(10) Patent No.: US 11,574,154 B2
(45) Date of Patent: Feb. 7, 2023

(54) PATIENT-ADAPTIVE NUCLEAR IMAGING

(71) Applicant: Siemens Medical Solutions USA, Inc., Malvern, PA (US)

(72) Inventors: Bruce S. Spottiswoode, Knoxville, TN (US); Juergen Soldner, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 17/650,738

(22) Filed: Feb. 11, 2022

(65) Prior Publication Data
US 2022/0164612 A1 May 26, 2022

Related U.S. Application Data

(62) Division of application No. 16/015,233, filed on Jun. 22, 2018, now abandoned.

(51) Int. Cl.
*G06K 9/62* (2022.01)
*G06T 7/215* (2017.01)
(Continued)

(52) U.S. Cl.
CPC ............ *G06K 9/6293* (2013.01); *A61B 6/032* (2013.01); *A61B 6/037* (2013.01); *A61B 6/5235* (2013.01);
(Continued)

(58) Field of Classification Search
None
See application file for complete search history.

(56) References Cited

U.S. PATENT DOCUMENTS

| 7,925,326 B2 | 4/2011 | Siegel et al. |
| 9,014,442 B2 | 4/2015 | Kelly et al. |

(Continued)

FOREIGN PATENT DOCUMENTS

| JP | 2010038594 A | 2/2010 | |
| JP | 2017086903 A | 5/2017 | |
| JP | 2017086903 A * | 5/2017 | ............. A61B 6/032 |

OTHER PUBLICATIONS

JP2017086903A translation (Year: 2022).*
(Continued)

*Primary Examiner* — Jason M Ip
*Assistant Examiner* — Renee C Langhals

(57) ABSTRACT

Systems and methods include control of a nuclear imaging scanner to acquire nuclear imaging scan data of a body, control of a computed tomography scanner to acquire computed tomography scan data of the body, determination of a scanning speed, of the nuclear imaging scanner, associated with each of a plurality of scanning coordinates based on locations of one or more internal volumes associated with radioactivity greater than a threshold level, a classification determined for each of the one or more of the internal volumes indicating a degree of clinical interest based at least in part on the radioactivity associated with the internal volume, and an attenuation coefficient map based on the computed tomography scan data, and control of the nuclear imaging scanner to scan the body over each of the scanning coordinates at the associated scanning speed.

20 Claims, 7 Drawing Sheets

(51) Int. Cl.
*G06T 7/37* (2017.01)
*A61B 6/03* (2006.01)
*A61B 6/00* (2006.01)

(52) U.S. Cl.
CPC .............. *A61B 6/544* (2013.01); *G06T 7/215* (2017.01); *G06T 7/37* (2017.01); *A61B 6/488* (2013.01); *G06T 2207/10081* (2013.01); *G06T 2207/10104* (2013.01)

(56) References Cited

U.S. PATENT DOCUMENTS

| | | |
|---|---|---|
| 9,053,569 B2 | 6/2015 | Bal et al. |
| 9,589,374 B1 | 3/2017 | Gao et al. |
| 2013/0105699 A1 | 5/2013 | Asma et al. |
| 2014/0321723 A1 | 10/2014 | Orcutt et al. |
| 2015/0063667 A1 | 3/2015 | Sprencz et al. |
| 2015/0379365 A1 | 12/2015 | Kelly et al. |
| 2017/0000448 A1* | 1/2017 | Hefetz ..................... A61B 6/52 |
| 2017/0042492 A1 | 2/2017 | Noshi |
| 2017/0164911 A1 | 6/2017 | Lv et al. |
| 2018/0303449 A1 | 10/2018 | Zhu et al. |

OTHER PUBLICATIONS

Sadik, May et al; "Improved classifications of planar whole-body bone scans using a computer-assisted diagnosis system: a multi-center, multiple-reader, multiple-case study"; Journal of nuclear medicine; 2009; vol. 50; No. 3; pp. 368-375.

\* cited by examiner

PATIENT-ADAPTIVE NUCLEAR IMAGING

CROSS-REFERENCE TO RELATED APPLICATIONS

This is a divisional application of U.S. patent application Ser. No. 16/015,233, filed Jun. 22, 2018, the contents of which are incorporated by reference herein for all purposes.

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

During an imaging process, the detector system is successively placed adjacent to portions of the body and detects gamma rays emitted from the body portions. Because the emissions occur over time, the duration for which a detector system is exposed to a body portion relates to the number of gamma rays detected from the body portion and, as a result, to the quality of the image reconstructed therefrom. However, the marginal benefit of extended exposure decreases with time, and it is also desirable to reduce overall acquisition time.

Conventional systems attempt to balance image quality and acquisition time by selecting from generic acquisition protocols which specify acquisition times for various body portions. In systems providing continuous bed motion, bed ranges and corresponding speeds are set to values which are believed to produce clinically-suitable images on a population average. What is needed are systems to efficiently determine and control scanning ranges and speeds based on anatomical structure and metabolic activity of a particular patient.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments determine image acquisition parameters that are specific to the anatomy and to the physiology of the patient being imaged. The acquisition parameter may include scanning speeds for various scanning ranges. An image is then acquired using the determined acquisition parameters. For a given acquisition time, embodiments may therefore provide higher-quality images with more clinical relevance than conventional nuclear imaging systems.

In one example, scanning speeds over different scanning ranges may be determined based on anatomical information provided by a computed tomography (CT) scan and on radiotracer distribution and uptake values provided by a nuclear imaging scan. This nuclear imaging scan may employ higher scanning speeds than a typical nuclear imaging scan because the signal-to-noise ratio of the image produced thereby is of less importance than it would be in the case of an image used for diagnosis.

Figure 1:
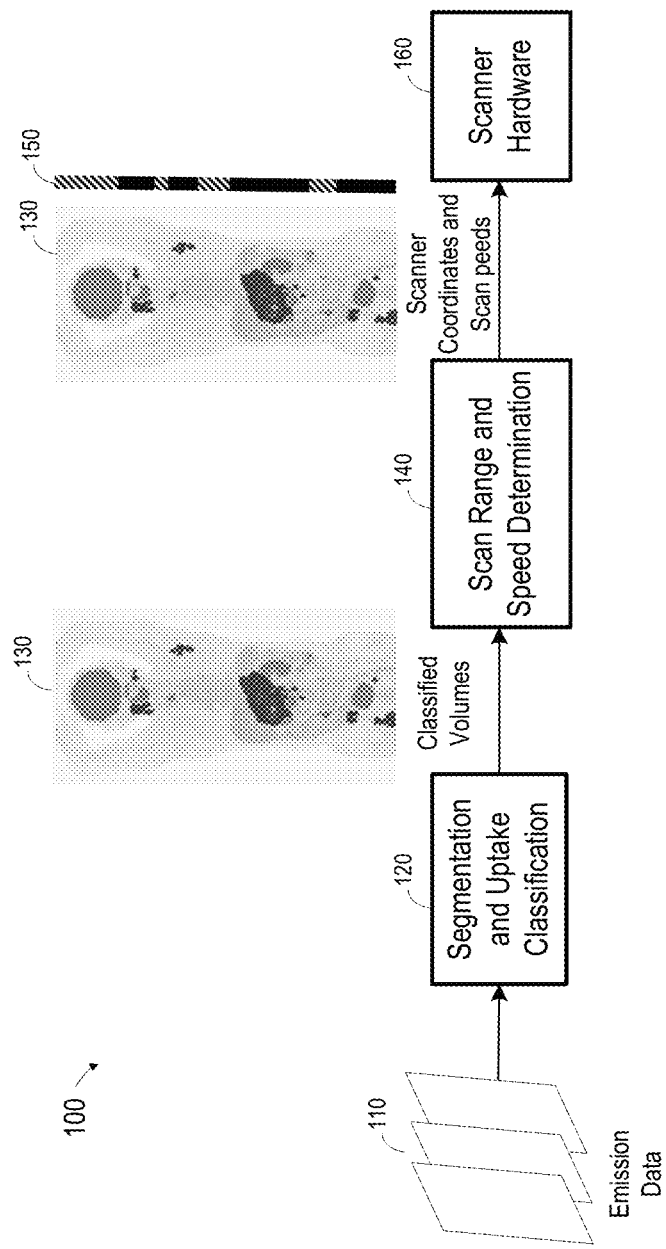
FIG. 1 is a block diagram of a system to perform adaptive scanning according to some embodiments.

FIG. 1 illustrates adaptive scanning according to some embodiments. Emission data 110 may comprise a plurality of sets of two-dimensional emission data generated by an emission imaging system during a scan of a body. As described above, such a system may comprise a SPECT system, a PET system, or another type of nuclear imaging system that is or becomes known. Emission data 110 may represent data which is typically reconstructed into volumetric image data as is known in the art.

Figure 2:
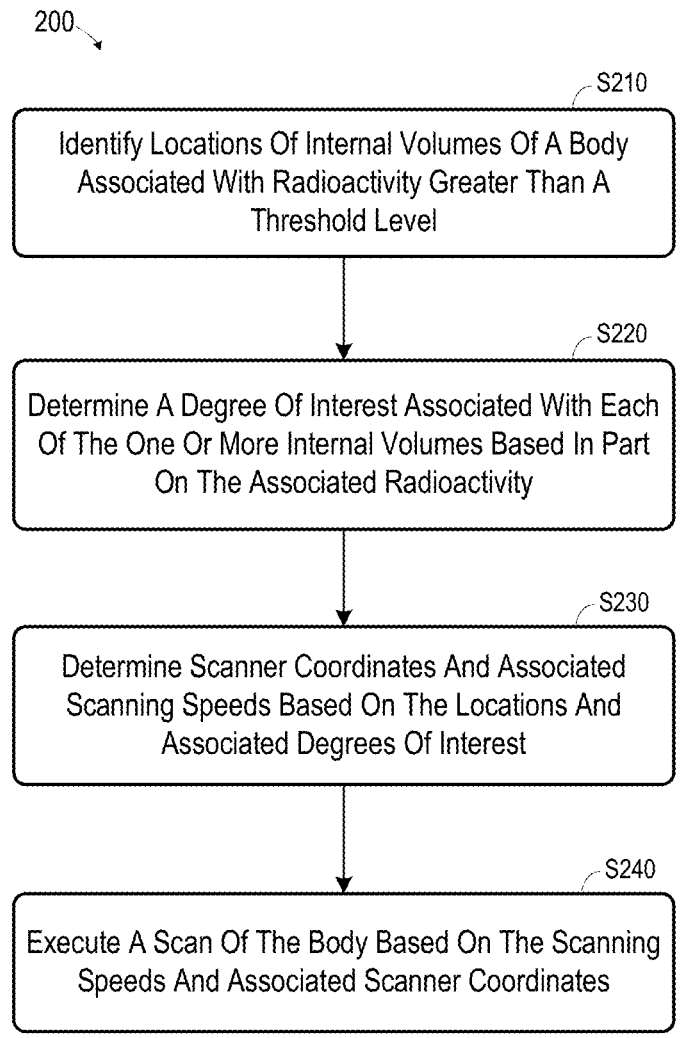
FIG. 2 is a flow diagram of a process to perform adaptive scanning according to some embodiments.

FIG. 2 is a flow diagram of process 200 depicted in FIG. 1 according to some embodiments. Process 200 and the other processes described herein may be performed using any suitable combination of hardware and software. Software program code embodying these processes may be stored by any non-transitory tangible medium, including a fixed disk, a volatile or non-volatile random access memory, a floppy disk, a CD, a DVD, a Flash drive, or a magnetic tape. Embodiments are not limited to the examples described below.

Based on emission data 110, segmentation and uptake classification component 120 may identify locations of internal volumes of the body at S210. The internal volumes may be those which are associated with a radioactivity greater than a threshold level. The radioactivity of a volume may be determined based on standard uptake values determined from emission data 110. Accordingly, S210 may comprise identification of locations of internal volumes associated with standard uptake values above a predefined threshold.

Component 120 also classifies each identified volume at S220 based at least in part on its radioactivity. The classification may associate an identified volume with a degree of clinical interest, and/or with one of a plurality of classifications, such as "physiological" or "suspicious". Graphic 130 represents thusly-classified volumes output by component 120 according to some embodiments, in which darker regions represent volumes classified as physiological and lighter regions represent volumes classified as suspicious. Embodiments may utilize any number or type of volume classifications. The output of component 120 may comprise three-dimensional coordinates representing locations of each identified internal volume, and metadata associating a classification with each identified volume.

Next, at S230, scan range and speed determination component 140 receives data representing the classified volumes from component 120. Based on the locations of the volumes and their respective classifications/degrees of interest, scan range and speed determination component 140 determines sets of scanner coordinates representing respective scanning ranges and, for each set of scanner coordinates, a scanning speed. A scanning speed may represent the speed of relative motion between the imaging detector and the body over the associated scanner coordinates. The sets of scanner coordinates and associated scanning speeds are parameters of an imaging scan.

Graphic 150 represents scanning ranges and speeds of an imaging scan determined based on the volumes and classifications depicted in graphic 130. According to the illustrated example, the hatched portions of graphic 150 indicate a "normal" scanning speed and the solid portions indicate a slower-than-normal scanning speed. Embodiments are not limited to two scanning speeds per scan, and any number of scan ranges may be used.

Generally, according to some embodiments, determination component 140 operates to determine slower scanning speeds for scan ranges corresponding to volumes which have been classified as suspicious or of greater clinical interest than for scan ranges corresponding to volumes which have been classified as physiological or of lesser clinical interest. A slower scanning speed allows for the detection of more gamma rays emitted by a volume over a scan range than a faster scanning speed, usually resulting in a better-quality image. A faster scanning speed may be used in regions of lesser interest, where image quality is of less concern. Embodiments are not limited to a single scan range or scan speed associated with each identified internal volume.

The determined scanner coordinates and speeds are provided to scanner hardware 160, which may operate to execute a scan at S240 based on these parameters. For example, scanner hardware 160 may perform the scan by causing relative movement between the detector(s) and each scanning range at the scanning speed associated with the scanning range. This movement may be performed by moving each scanning range past the detector(s) (e.g., by moving a bed on which a patient rests), by moving the detector in the scanning direction, or by a combination of both types of movement. Embodiments may thereby efficiently and automatically provide suitable images of clinically-important areas while reducing overall scanning time.

Segmentation and uptake classification component 120, scan range and speed determination component 140, and each functional component described herein may be implemented at least in part in computer hardware, in program code and/or in one or more computing systems executing such program code as is known in the art. Such a computing system may include one or more processing units which execute processor-executable program code stored in a memory system.

Figure 3:
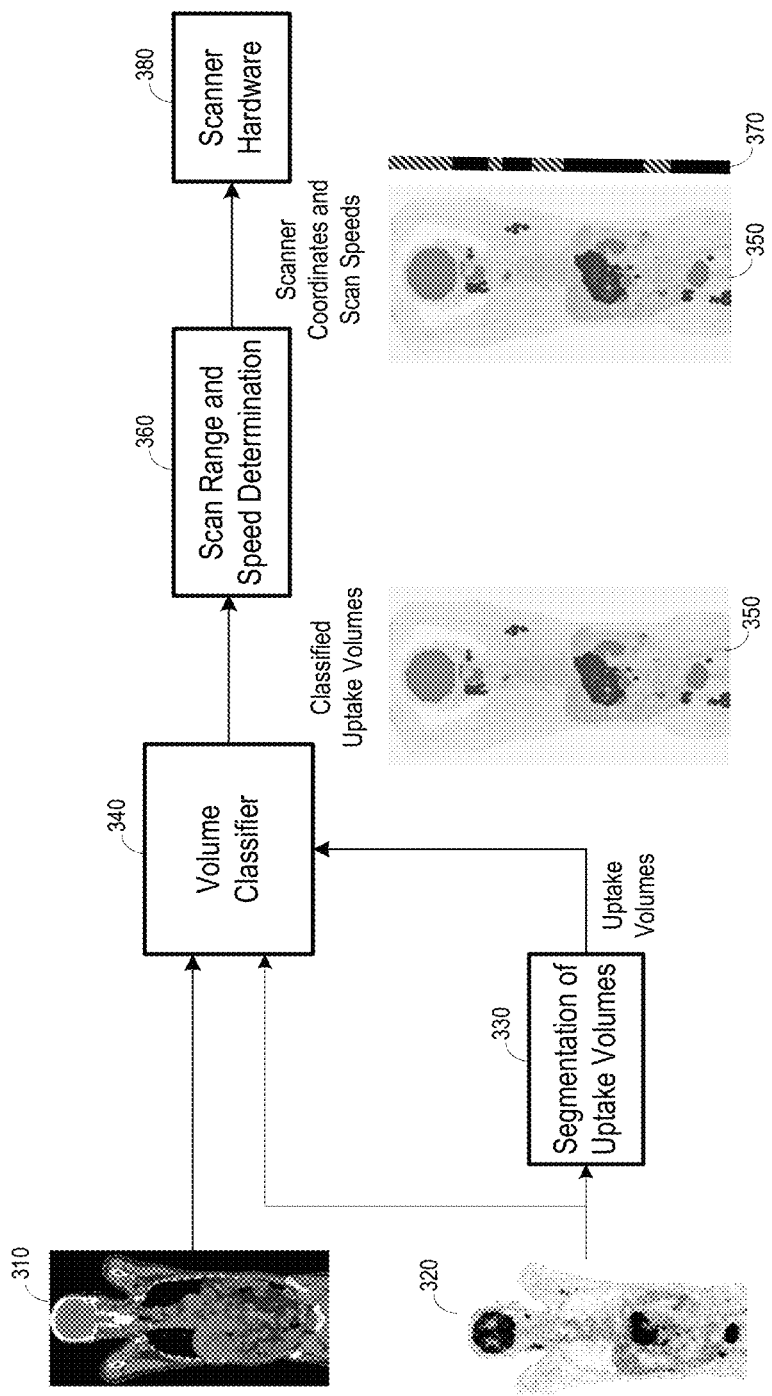
FIG. 3 is a block diagram of a system to perform adaptive scanning based on a CT scan and a PET scan according to some embodiments.

FIG. 3 illustrates adaptive scanning based on a CT scan and a PET scan according to some embodiments. Generally, CT image 310 provides anatomical information and PET image 320 provides radiotracer distribution and uptake values, both of which are used to determine scanner coordinates and respective scanning speeds to be used during a subsequent PET scan. The scanning depicted in FIG. 3 may comprise an implementation of process 200 but embodiments are not limited thereto.

As illustrated, component 330 receives PET image 320 and segments uptake volumes based thereon. PET image 320 indicates standard uptake values as is known in the art, and known algorithms may be applied to PET image 320 to identify various volumes of the imaged body which are associated with standard uptake values greater than a threshold. Different thresholds may be used for different body regions, and may depend on background activity in a local organ or volume. In one example, U.S. Pat. No. 9,014,442 to Kelly et al. describes the identification of volumes of interest based on standard uptake values, although embodiments are not limited thereto.

PET image 320 may comprise a "PET scout", which was acquired at a higher scanning speed than a typical nuclear imaging scan. The higher scanning speed may result in a lower signal-to-noise ratio within PET image 320 than would be achieved at lower scanning speeds. However, the lower signal-to-noise ratio does not appreciably affect the determination of uptake volumes in some embodiments, while allowing the entire process of FIG. 3 to be completed in significantly less time than if PET image 320 was acquired at a conventional scanning speed.

CT image 310 may be acquired substantially contemporaneously with the acquisition of PET image 320. For example, a CT imaging system of a PET/CT scanner may be operated to acquire CT image 310 while a patient lies in a given position on a bed of the PET/CT scanner, and a PET imaging system of the PET/CT scanner may be operated immediately thereafter to acquire PET image 320 while the patient remains on the bed in the given position. Anatomical information determined from CT image 310 may be used to plan acquisition (e.g., an overall scanning range) of PET image 320. Also, and because the geometric transformation (if any) between coordinates of the CT scanner and the PET scanner is known, CT image 310 and PET image 320 may be consider as substantially registered with one another.

CT image 310, PET image 320, and data describing the boundaries of segmented uptake volumes are input to volume classifier 340. Volume classifier 340 may associate each uptake volume with one of two or more classifications. The classifications may indicate a degree of clinical interest of an uptake volume as described above. Graphic 350 represents uptake volumes and their classifications as output by volume classifier 340. According to some embodiments, volume classifier 340 receives one or more additional inputs such as but not limited to genomic information, laboratory results (e.g., from a blood sample), family history, and information describing therapy applied between a prior scan and a current scan.

Volume classifier 340 may comprise a trained neural classification network in some embodiments. One example of such a network is described in U.S. Patent Application Publication No. 2015/0379365. Generally, volume classifier 340 may comprise a classification network to classify uptake volumes, and which was trained based on labeled sets of data, where each set of data includes a CT image, a contemporaneous PET image, data describing segmented uptake volumes of the PET image, and classifications of each of the segmented uptake volumes.

Scan range and speed determination component 360 receives data representing the classified volumes from volume classifier 340. As described above, scan range and speed determination component 360 uses the received data to determine sets of scanner coordinates representing respective scanning ranges and, for each set of scanner coordinates, a scanning speed. Graphic 370 represents scanning ranges and speeds of an imaging scan determined based on the volumes and classifications depicted in graphic 350. As above, the hatched portions of graphic 150 indicate a "normal" scanning speed and the solid portions indicate a slower-than-normal scanning speed.

The determined scanner coordinates and speeds are provided to scanner hardware 160, which may operate to execute a PET scan based on these parameters. For example, scanner hardware 160 may support continuous bed motion scanning, and may perform the PET scan by moving its bed so as to move each scanning range of the body between the detectors of its PET scanner at the scanning speed associated with the scanning range.

Figure 4:
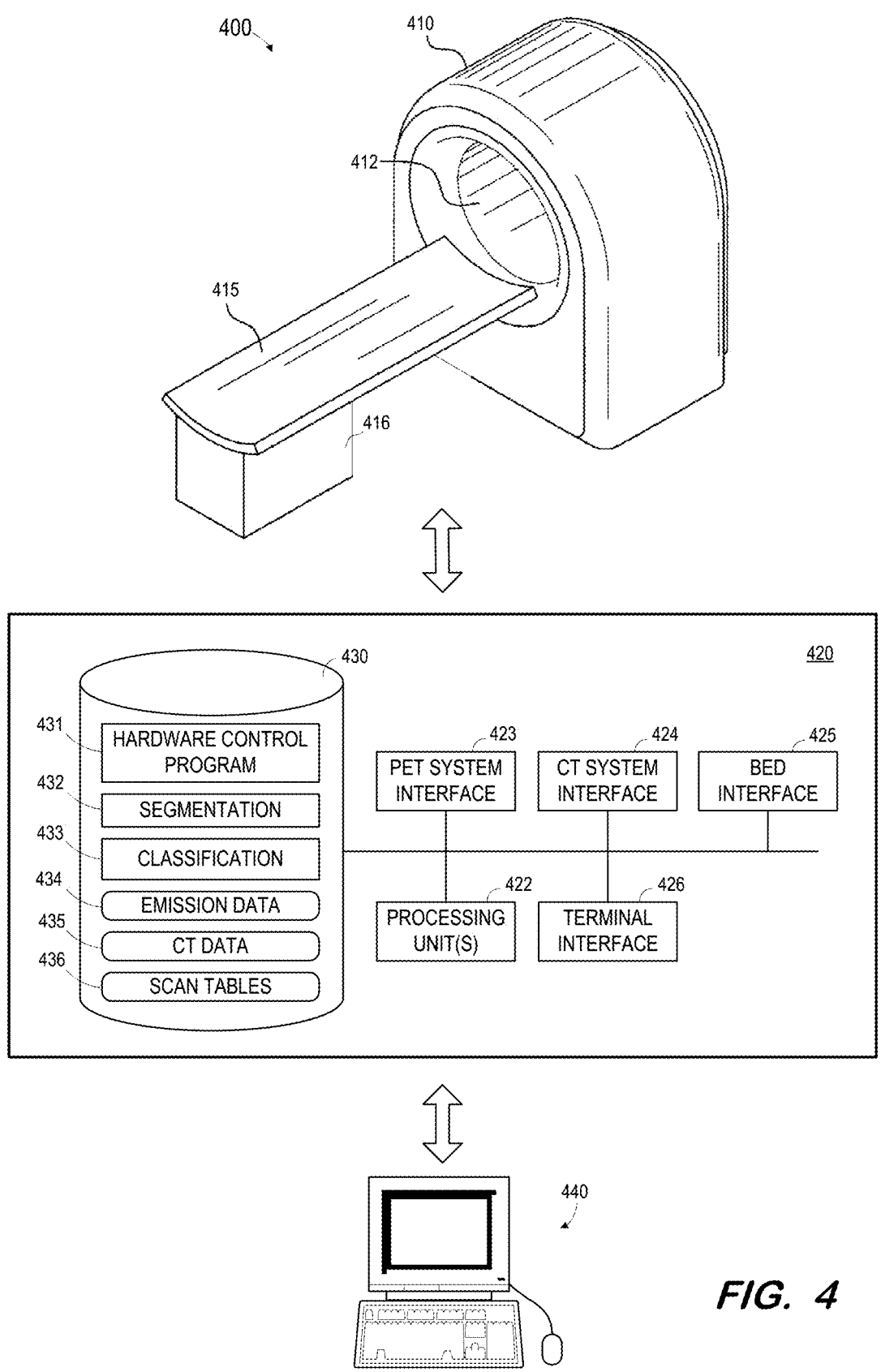
FIG. 4 illustrates an imaging system according to some embodiments.

FIG. 4 illustrates PET/CT system 400 to execute one or more of the processes described herein. Embodiments are not limited to system 400.

System 400 includes gantry 410 defining bore 412. As is known in the art, gantry 410 houses PET imaging components for acquiring PET image data and CT imaging components for acquiring CT image data. The PET imaging components may include any number of gamma cameras in any configuration as is known in the art. The CT imaging components may include one or more x-ray tubes and one or more corresponding x-ray detectors.

Bed 415 and base 416 are operable to move a patient lying on bed 415 into and out of bore 412. In some embodiments, bed 415 is configured to translate over base 416 and, in other embodiments, base 416 is movable along with or alternatively from bed 415.

Movement of a patient into and out of bore 412 may allow scanning of the patient using the CT imaging elements and PET imaging elements of gantry 410. Such scanning may proceed based on scanning parameters such as scan ranges and corresponding scanning speeds. Bed 415 and base 416 may provide continuous bed motion, as opposed to step-and-shoot motion, during such scanning according to some embodiments.

Control system 420 may comprise any general-purpose or dedicated computing system. Accordingly, control system 420 includes one or more processing units 422 configured to execute processor-executable program code to cause system 420 to operate as described herein, and storage device 430 for storing the program code. Storage device 430 may comprise one or more fixed disks, solid-state random access memory, and/or removable media (e.g., a thumb drive) mounted in a corresponding interface (e.g., a USB port).

Storage device 430 stores program code of hardware control program 431. One or more processing units 422 may execute hardware control program 431 to, in conjunction with PET system interface 423 and bed interface 425, control hardware elements to move a patient into bore 412 and, during the movement, control gamma cameras to rotate around bore 412 and to acquire two-dimensional emission data of a body located in bore 412 at defined imaging positions during the rotation. The movement may be based on scanning ranges and corresponding scanning speeds determined as described herein. The acquired data may be stored in memory 430 as emission data 434.

One or more processing units 422 may also execute hardware control program 431 to, in conjunction with CT system interface 424, cause a radiation source within gantry 410 to emit radiation toward a body within bore 412 from different projection angles, and to control a corresponding detector to acquire two-dimensional CT data. The CT data may be acquired substantially contemporaneously with the emission data as described above, and the may be stored as CT data 435.

Segmentation program 432 may be executed to segment uptake volumes of emission data 434 as described above. Similarly, classification program 433 may be executed to classify the segmented uptake volumes. As described above, the classification may be based on the segmented uptake volumes, emission data 434, and corresponding CT data 435.

Storage device 430 also includes scan tables 436 according to some embodiments. As will be described below, scan tables may associate a particular diagnosis (e.g., prostate cancer) with organ or anatomical regions, and each such region with a scanning speed. The information of scan tables 436 may therefore be used to inform the determination of scan ranges and scanning speeds described herein.

A PET image acquired based on determined scanning ranges and scanning speeds may be transmitted to terminal 440 via terminal interface 426. Terminal 440 may comprise a display device and an input device coupled to system 420. Terminal 440 may display PET scout images, CT images, PET images acquired based on scanning ranges and scanning speeds determined as described herein, uptake volumes, uptake volume classifications, and/or any other suitable images or data. Terminal 440 may receive user input for controlling display of the data, operation of system 400, and/or the processing described herein. In some embodiments, terminal 440 is a separate computing device such as, but not limited to, a desktop computer, a laptop computer, a tablet computer, and a smartphone.

Each of component of system 400 may include other elements which are necessary for the operation thereof, as well as additional elements for providing functions other than those described herein.

Figure 5:
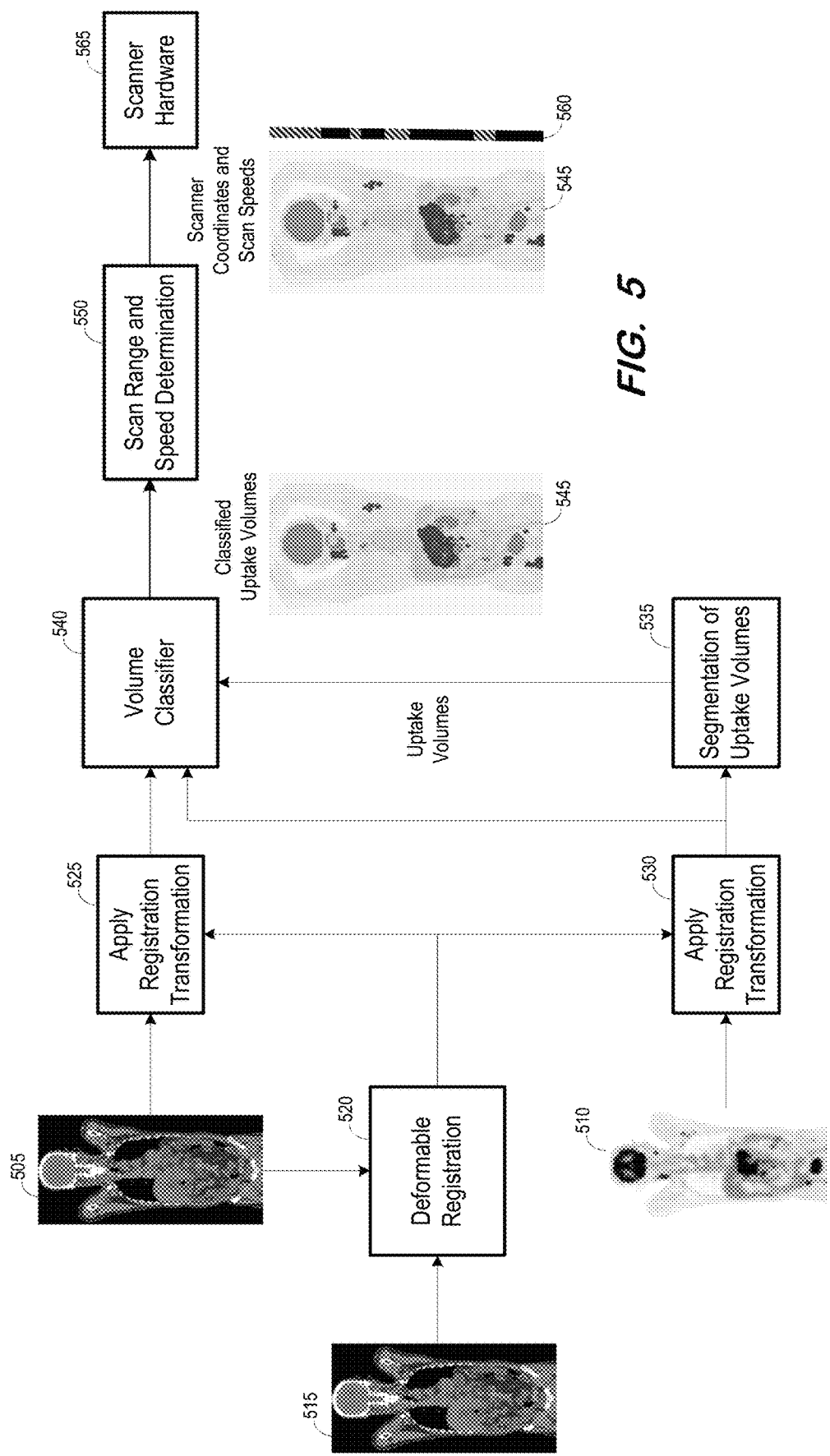
FIG. 5 is a block diagram of a system to perform adaptive scanning based on previously-acquired CT and PET scans according to some embodiments.

FIG. 5 illustrates a system using previously-acquired PET and CT data to determine scanning ranges and scanning speeds according to some embodiments. In particular, CT image 505 and PET image 510 are acquired during a same imaging visit/session (e.g., immediately following one another, during a prior scan), and CT image 515 is acquired at a future date (e.g., during the "current" session). PET image 510 may comprise a high-quality diagnostic PET image or a PET scout image as described above.

After acquisition of CT image 515, using for example a system such as system 400, deformable registration component 520 performs deformable registration of CT images 505 and 515 as is known in the art. Assuming that image 505 and image 510 are substantially registered with one another, the deformable registration produces a registration transformation of deformation fields from the prior image to the current image. The registration transformation is applied 525 to CT image 505 and is applied 530 to PET image 510 in order to register the images to the coordinate system of current CT image 515.

The process may then proceed as previously described. Specifically, component 535 receives the registered version of PET image 510 and segments uptake volumes based thereon. Volume classifier 540 associates each uptake volume with one of two or more classifications based on registered CT image 505, registered PET image 510, and data 545 describing the boundaries of segmented uptake volumes. According to some embodiments, the operation of component 535 and classifier 540 may be replaced by manual identification and classification of uptake volumes by a human expert based on registered CT image 505 and registered PET image 510. The manual identification and classification may alternatively be conducted in parallel with the operation of component 535 and classifier 540 in order to further inform the determination of component 550.

Scan range and speed determination component 550 receives data representing the classified volumes from volume classifier 540, and uses the received data to determine sets of scanner coordinates representing respective scanning ranges and, for each set of scanner coordinates, a scanning speed, as depicted in graphic 545. The determined scanner coordinates and speeds are provided to scanner hardware 565, which executes a PET scan based thereon.

Figure 6:
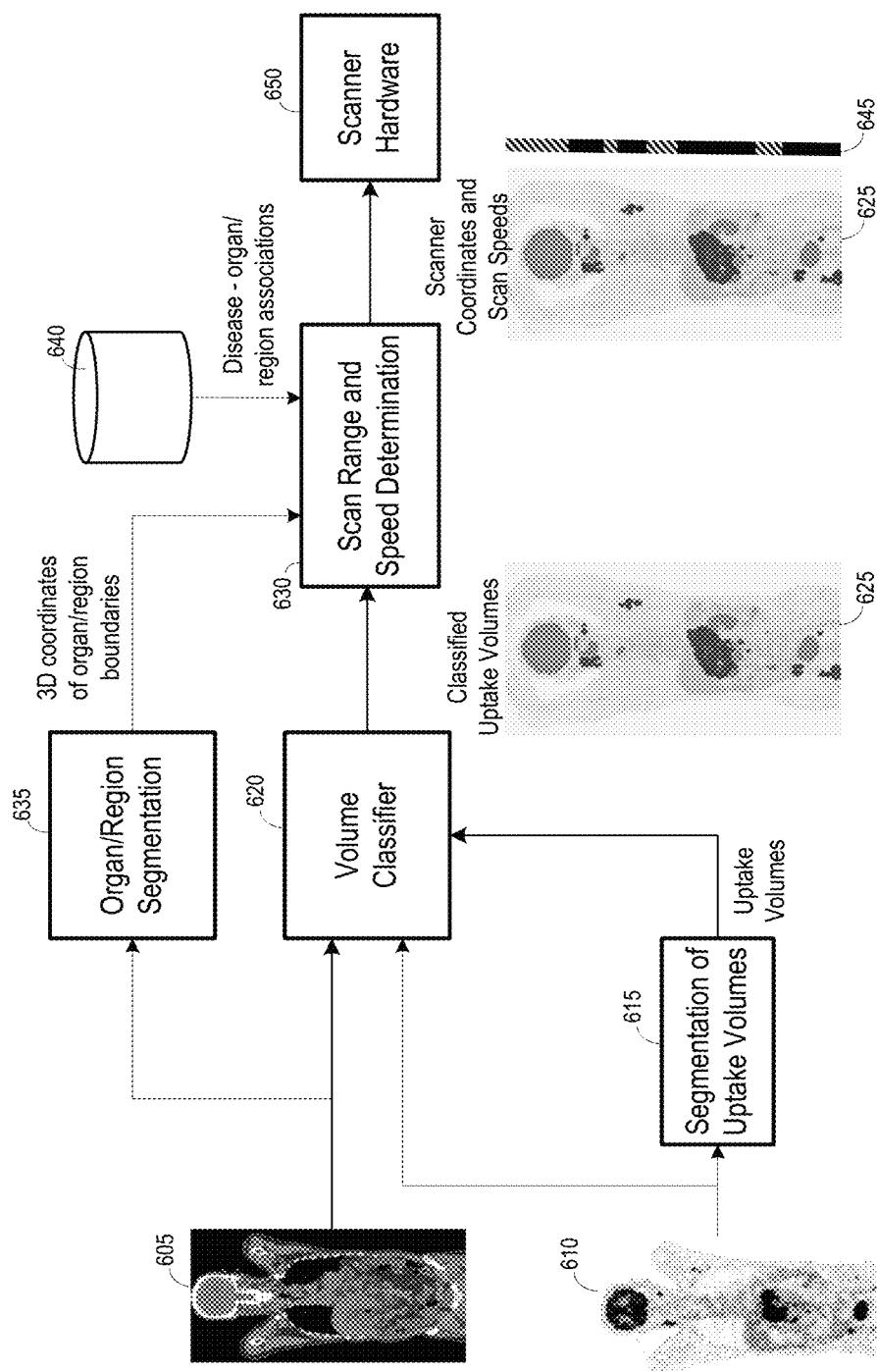
FIG. 6 is a block diagram of a system to perform adaptive scanning based on a CT scan, a PET scan and data associating organ boundaries with scanning speeds according to some embodiments.

FIG. 6 illustrates an implementation similar to the implementation of FIG. 3, but including organ/region segmentation component 635. Component 635 generates, based on CT image 605, three-dimensional coordinates of organ and/or region boundaries. Such segmentation is known in the art, and may include use of a trained neural network.

FIG. 6 also depicts data 640 which may comprise a preconfigured scan table of associations between diseases and organs/anatomical regions, and a scan speed for each organs/anatomical region associated with a particular disease. Example regions may include distinct organs, lymph node stations, or arbitrary combinations of anatomical landmarks. Scan range and speed determination component 630 therefore receives data representing the classified volumes from volume classifier 620, three-dimensional coordinates of organ and/or region boundaries from segmentation component 635, and disease/region/scan speed associations from data 640.

The sets of scanner coordinates and scanning speeds may be determined based on these inputs using any suitable algorithm. In some embodiments, the determination consists of identifying a disease of interest (e.g., via user input into terminal 440), determining organs and regions associated with the disease from data 640, determining scan ranges associated with these organs and regions based on the three-dimensional boundary coordinates, and associating a scan speed with each scan range based on the scan speed associated with the corresponding organ/region in data 640. The assigned speeds may then be modified based on the classifications of the uptake volumes corresponding to each region. For example, if data 640 associates a normal scan speed with a particular region but the uptake volume associated with the region is identified as suspicious, component 630 may determine a slower-than-normal scan speed for the scan range associated with the region.

Figure 7:
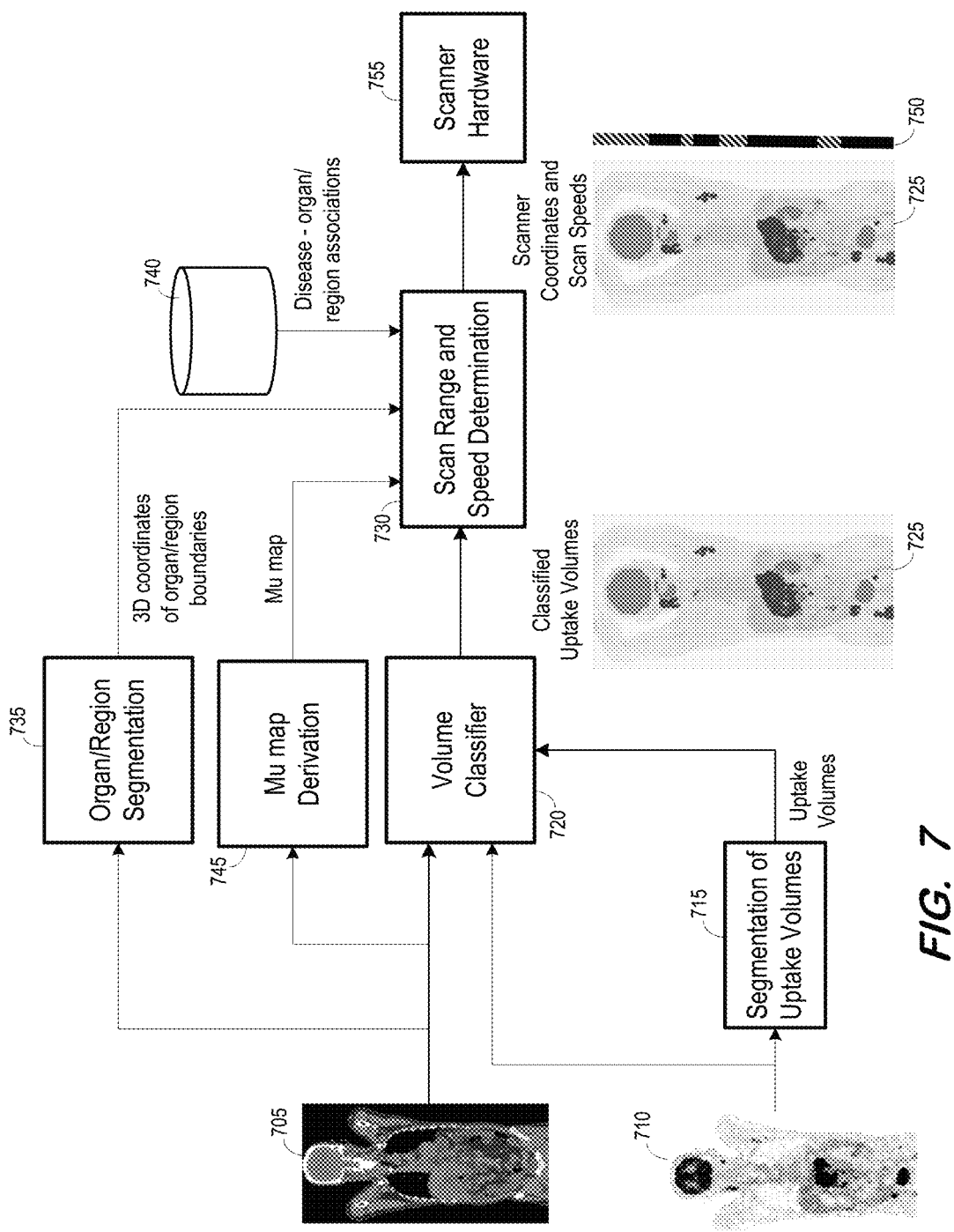
FIG. 7 is a block diagram of a system to perform adaptive scanning based on a CT scan, a PET scan, data associating organ boundaries with scanning speeds, and an attenuation coefficient map according to some embodiments.

FIG. 7 illustrates an implementation which is similar to the FIG. 6 implementation and in which Mu map derivation component 745 derives a Mu map (e.g., an attenuation coefficient map) from CT image 705 as is known in the art. The Mu map is provided as a fourth input to scan range and speed determination component 730 as illustrated. Embodiments may incorporate any combination of these four and other inputs to component 730. Component 730 may utilize the Mu map to adjust scan speeds to compensate for gamma ray attenuation. For example, greater attenuation may reduce counts and require slower scan speeds.

Some embodiments described above include acquisition of a PET scout image and a CT image. The PET scout image may be acquired prior to the CT image for quality assurance purposes. For example, the PET scout image may be used to determine whether the patient is moving or failed to fast, causing unwanted absorption of the radioactive tracer. If so, the imaging process may be aborted so as not to subject the patient to an unnecessary CT scan.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a nuclear imaging scanner to acquire nuclear imaging scan data of a body;
   a computed tomography scanner to acquire computed tomography scan data of the body; and
   a processing system to:
   identify one or more internal volumes of the body based on the nuclear imaging scan data, each of the one or more internal volumes associated with radioactivity greater than a threshold level;
   for each of the one or more internal volumes, determine a classification indicating a degree of clinical interest based at least in part on the radioactivity associated with the internal volume;
   generate an attenuation coefficient map based on the computed tomography scan data;
   determine a scanning speed, of the nuclear imaging scanner, associated with each of a plurality of scanning coordinates based on locations of the one or more internal volumes, the classification determined for each of the one or more of the internal volumes, and the attenuation coefficient map; and
   control the nuclear imaging scanner to scan the body based on the scanning speed associated with each of the plurality of scanning coordinates.

2. The system according to claim 1, wherein the nuclear imaging scanner is to perform a scout scan to acquire the nuclear imaging scan data of the body.

3. The system according to claim 1, wherein the classification determined for each of the one or more internal volumes is determined based on the computed tomography scan data and the nuclear imaging scan data.

4. The system according to claim 3, further comprising:
   a memory system to store data associating anatomical regions with scanning speeds;
   the processing system further to:
   segment the computed tomography scan data to acquire three-dimensional coordinates of anatomical region boundaries,
   wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and the data associating anatomical regions with scanning speeds.

5. The system according to claim 4, wherein identification of the one or more internal volumes of the body comprises segmentation of the nuclear imaging scan data.

6. The system according to claim 1, further comprising:
   a memory system to store data associating anatomical regions with scanning speeds;
   the processing system further to:
   segment the computed tomography scan data to acquire three-dimensional coordinates of anatomical region boundaries,
   wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and the data associating anatomical regions with scanning speeds.

7. The system according to claim 1, the processing system further to:
   register the computed tomography scan data against previously-acquired computed tomography scan data of the body to determine a registration transformation;

apply the registration transformation to previously-acquired nuclear imaging scan data of the body to generate transformed nuclear imaging scan data of the body, the previously-acquired nuclear imaging scan data being temporally and spatially associated with the previously-acquired computed tomography scan data; and apply the registration transformation to the previously-acquired computed tomography scan data of the body to generate transformed computed tomography scan data of the body;

wherein the one or more internal volumes are identified based on the transformed nuclear imaging scan data of the body, and wherein the classification determined for each of the one or more internal volumes is determined based at least in part on the transformed computed tomographyscan data and the one or more internal volumes.

8. A method comprising:

controlling a nuclear imaging scanner to acquire nuclear imaging scan data of a body;

controlling a computed tomography scanner to acquire computed tomography scan data of the body;

identifying one or more internal volumes of the body based on the nuclear imaging scan data, each of the one or more internal volumes associated with radioactivity greater than a threshold level;

for each of the one or more internal volumes, determining a classification indicating a degree of clinical interest based at least in part on the radioactivity associated with the internal volume;

generating an attenuation coefficient map based on the computed tomography scan data;

determining a scanning speed, of the nuclear imaging scanner, associated with each of a plurality of scanning coordinates based on locations of the one or more internal volumes, the classification determined for each of the one or more of the internal volumes, and the attenuation coefficient map; and controlling the nuclear imaging scanner to scan the body over each of the plurality of scanning coordinates at the associated scanning speed.

9. The method according to claim 8, wherein controlling the nuclear
imaging scanner to acquire nuclear imaging scan data of the body comprises controlling the
nuclear imaging scanner to perform a scout scan of the body.

10. The method according to claim 8, wherein the classification
determined for each of the one or more internal volumes is determined based on the computed
tomography scan data and the nuclear imaging scan data.

11. The method according to claim 10, further comprising:

segmenting the computed tomography scan data to acquire three-dimensional coordinates of anatomical region boundaries, wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and stored data associating anatomical regions with scanning speeds.

12. The method according to claim 11, wherein identifying the one or
more internal volumes of the body comprises segmenting the nuclear imaging scan data.

13. The method according to claim 8, further comprising:

segmenting the computed tomography scan data to acquire three-dimensional coordinates of anatomical region boundaries, wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and the data associating anatomical regions with scanning speeds.

14. The method according to claim 8, further comprising:

registering the computed tomography scan data against previously-acquired computed tomography scan data of the body to determine a registration transformation;

applying the registration transformation to previously-acquired nuclear imaging scan data of the body to generate transformed nuclear imaging scan data of the body, the previously-acquired nuclear imaging scan data being temporally and spatially associated with the previously-acquired computed tomography scan data; and applying the registration transformation to the previously-acquired computed tomography scan data of the body to generate transformed computed tomography scan data of the body;

wherein the one or more internal volumes are identified based on the transformed nuclear imaging scan data of the body, and wherein the classification determined for each of the one or more internal volumes is determined based at least in part on the transformed computed tomography scan data and the one or more internal volumes.

15. A non-transitory medium storing program code executable by a processor
of a computing system to cause the computing system to:

control a nuclear imaging scanner to acquire nuclear imaging scan data of a body;

control a computed tomography scanner to acquire computed tomography scan data of the body;

identify one or more internal volumes of the body based on the nuclear imaging scan data, each of the one or more internal volumes associated with radioactivity greater than a threshold level;

for each of the one or more internal volumes, determine a classification indicating a degree of clinical interest based at least in part on the radioactivity associated with the internal volume;

generate an attenuation coefficient map based on the computed tomography scan data;

determine a scanning speed, of the nuclear imaging scanner, associated with each of a plurality of scanning coordinates based on locations of the one or more internal volumes, the classification determined for each of the one or more of the internal volumes, and the attenuation coefficient map; and control the nuclear imaging scanner to scan the body over each of the plurality of scanning coordinates at the associated scanning speed.

16. The non-transitory medium according to claim 15, wherein control of the nuclear imaging scanner to acquire nuclear imaging scan data of the body comprises control of the nuclear imaging scanner to perform a scout scan of the body.

17. The non-transitory medium according to claim 15, wherein the
classification determined for each of the one or more internal volumes is determined based on
the computed tomography scan data and the nuclear imaging scan data.

18. The non-transitory medium according to claim 17, the program code
executable by a processor of a computing system to cause the computing system to:
segment the computed tomography scan data to acquire three-dimensional coordinates of anatomical region boundaries,
wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and stored data associating anatomical regions with scanning speeds.

19. The non-transitory medium according to claim 15, the program code
executable by a processor of a computing system to cause the computing system to:
segment the computed tomography scan data to acquire three-dimensional coordinates of anatomical region boundaries,
wherein the scanning speed associated with each of the plurality of scanning coordinates is determined based at least in part on the locations of the one or more internal volumes, the degree of clinical interest associated with each of the one or more of the internal volumes, the three-dimensional coordinates of anatomical region boundaries, and the data associating anatomical regions with scanning speeds.

20. The non-transitory medium according to claim 15, the program code
executable by a processor of a computing system to cause the computing system to:
register the computed tomography scan data against previously-acquired computed tomography scan data of the body to determine a registration transformation;
apply the registration transformation to previously-acquired nuclear imaging scan data of the body to generate transformed nuclear imaging scan data of the body, the previously-acquired nuclear imaging scan data being temporally and spatially associated with the previously-acquired computed tomography scan data; and
apply the registration transformation to the previously-acquired computed tomography scan data of the body to generate transformed computed tomography scan data of the body;
wherein the one or more internal volumes are identified based on the transformed nuclear imaging scan data of the body, and
wherein the classification determined for each of the one or more internal volumes is determined based at least in part on the transformed computed tomography scan data and the one or more internal volumes.

* * * * *